United States Patent [19]

Bertozzi

[11] 4,131,716

[45] Dec. 26, 1978

[54] ACRYLIC ACID ESTERS OF POLYTHIODIALKANOLS AND RELATED COMPOUNDS

[75] Inventor: Eugene R. Bertozzi, Yardley, Pa.

[73] Assignee: Thiokol Corporation, Newtown, Pa.

[21] Appl. No.: 791,756

[22] Filed: Apr. 28, 1977

[51] Int. Cl.$^2$ ............................. C08F 2/50; C08F 4/00
[52] U.S. Cl. .................. 428/425; 204/159.23; 260/885; 427/54; 428/522; 526/311; 560/222
[58] Field of Search .................. 427/54; 204/159.15, 204/159.23; 560/222; 428/425, 522

[56] References Cited

U.S. PATENT DOCUMENTS

| | | | |
|---|---|---|---|
| 2,221,418 | 11/1940 | Weihe | 260/755 |
| 3,415,764 | 12/1968 | Erickson | 560/222 X |
| 3,716,466 | 2/1973 | Hook | 204/159.17 |
| 3,850,770 | 11/1974 | Juna et al. | 204/159.19 |
| 4,039,723 | 8/1977 | Moyer et al. | 204/159.15 X |

FOREIGN PATENT DOCUMENTS 264392  6/1970  U.S.S.R. .................................. 560/222

*Primary Examiner*—Walter C. Danison
*Attorney, Agent, or Firm*—Stanley A. Marcus; Royal E. Bright

[57] ABSTRACT

Diacrylate esters of dithiodiglycol and of polyether and polyformal oligomers thereof, their preparation, and use in combination with other radiation curable prepolymers for preparation of radiation curable compositions are disclosed.

3 Claims, No Drawings

ACRYLIC ACID ESTERS OF POLYTHIODIALKANOLS AND RELATED COMPOUNDS

BACKGROUND OF THE INVENTION

The ability of the disulfide bond to cleave when subjected to radiation of the appropriate wavelength and to serve as a photo initiator in preparing block copolymers with polyether urethanes and vinyl monomers has been reported by Fildes and Tobolsky in *Journal of Polymer Science:* Part A-1, Vol. 10, pp 151–161, (1972).

The present invention is related to the use of acrylate esters of dithiodiglycol [bis($\beta$-hydroxyethyl disulfide)], and of polyether and polyformal oligomers thereof as reactive diluents for conventional ultraviolet curable polyurethane prepolymer based systems, as well as, of course, to the novel compounds themselves and the novel curable systems produced through their use.

SUMMARY OF THE INVENTION

The invention provides in a composition aspect a compound of the formula:

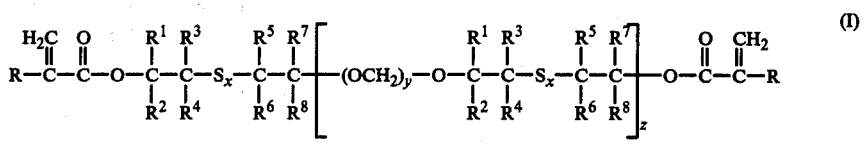
(I)

wherein R is hydrogen or methyl, $R^1$, $R^2$, $R^3$, $R^4$, $R^5$, $R^6$, $R^7$ and $R^8$ are hydrogen, methyl, or ethyl or independently are hydrogen, methyl, ethyl, or chloromethyl; $x$ is from about 2 to about 4; $y$ is 0 or an integer of from 1 to about 3; and $z$ is 0 or a number sufficient to make a total average molecular weight of up to about 4000.

The tangible embodiments of this composition aspect of the invention possess the inherent applied use characteristic of being liquids curable to solids upon exposure to actinic radiation in the ultraviolet region of the electromagnetic spectrum, thus evidencing their usefulness in the preparation of cured films and coatings for printing, wood finishing, floor tile and the like. The tangible embodiments wherein $z$ is 0 are also low viscosity materials which are useful as reactive diluents for acrylate terminated urethane prepolymer systems to reduce their viscosity and to provide additional extensibility and flexibility to UV cured films prepared therefrom.

Preferred embodiments of this composition aspect of the invention are compounds of Formula I wherein $z$ is 0.

The invention also provides a curable composition which comprises:
(a) an acrylate terminated polyurethane prepolymer;
(b) a compound of Formula I; and
(c) a photosensitizer.

The invention also provides a process for the preparation of a UV curable composition based on an acrylate terminated polyurethane prepolymer, having improved extensibility and flexibility in the cured state which comprises blending:
(a) an acrylate terminated polyurethane prepolymer;
(b) a compound of Formula I; and
(c) a photosensitizer.

The invention also provides an article of manufacture which comprises a substrate coated on at least one surface with a coating comprising the actinic radiation induced reaction products of
(a) an acrylate terminated polyurethane prepolymer;
(b) a compound of Formula I; and
(c) a photosensitizer.

DESCRIPTION OF THE PREFERRED EMBODIMENTS

A method for the preparation of compounds of Formula I will now be illustrated with reference to a specific embodiment thereof namely dithiodiglycol diacrylate (II).

To prepare II, dithiodiglycol is treated with an excess of ethyl acrylate in the presence of polymerization inhibitors and a transesterification catalyst while heating at a temperature sufficient to cause liberated ethanol to distill until such time as ethanol ceases to be evolved. Phenothiazine and nitrobenzene are convenient as polymerization inhibitors, and bleeding air through the reaction is also a convenient inhibition method, although any inhibitor known in the art will obviously be useful. Any known transesterification catalyst may also be employed. Tyzor TPT (Triisopropyl Titanate) is a particularly convenient catalyst. The reaction may be performed neat using an excess of acrylic ester as the solvent, or, if desired, an inert solvent may be employed. The exact time and temperature for the reaction are not especially critical. A temperature just sufficient to cause the alcohol liberated from the acrylic ester during the course of the reaction to distill without causing excessive vaporization of the reactants will obviously be desirable. The reaction may be continued until it is determined that substantially all such liberated alcohol has been removed from the reaction and that further substantial quantities are no longer evolved.

One skilled in the art wil recognize that other known acrylate or methacrylate esters may be employed in analogous fashion to the ethyl acrylate illustrated as full equivalents thereto for the preparation of the compounds of Formula I.

One skilled in the art will also recognize that, although the preparation of compounds of Formula I was illustrated through the use of dithiodiglycol,

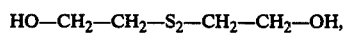

one may also substitute other monomeric polythiodiglycols in analogous reactions to prepare the other monomeric compounds of Formula I.

These polythiodiglycols have the structure:

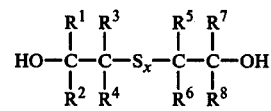

wherein $R^1$, $R^2$, $R^3$, $R^4$, $R^5$, $R^6$, $R^7$, $R^8$ and $x$ are as defined hereinabove. Suitable manufacturing methods for these polythiodiglycols are disclosed in U.S. Pat. No. 2,754,333 and German Pat. No. 1,093,790.

Polymerization to an ether polymer (to prepare compounds of Formula I of z up to about 4000 M.W., y=0) may be effected by polyetherification as illustrated

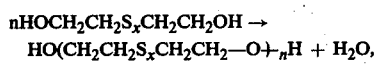
$$nHOCH_2CH_2S_xCH_2CH_2OH \rightarrow$$
$$HO(CH_2CH_2S_xCH_2CH_2-O)_nH + H_2O,$$

or to a polyformal by copolymerization with formaldehyde (to prepare polyformals of Formula I of z up to a molecular weight of about 4000, y = 1, 2 or 3) as illustrated

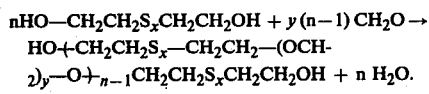
$$nHO-CH_2CH_2S_xCH_2CH_2OH + y(n-1)CH_2O \rightarrow$$
$$HO+CH_2CH_2S_x-CH_2CH_2-(OCH_2)_y-O+_{n-1}CH_2CH_2S_xCH_2CH_2OH + n H_2O.$$

In both cases an acid catalyst is employed, as well as a standard means of removing the water of reaction until the desired molecular weight level is achieved.

In using the compositions of the invention the compounds of Formula I may either be applied themselves as a coating on a substrate and cured by application of actinic radiation preferably ultraviolet light either without or preferably with the incorporation of a photoinitiator in the usual fashion. Obviously other, non-opaque to the particular radiation used, conventional fillers and additives may also be employed as desired. The application may be with or without the aid of a volatile solvent as may be found convenient in a particular application.

The compounds of Formula I may also be employed as reactive diluents in conventional known actinic radiation curable systems formulated from known polyurethane based acrylate terminated prepolymers.

These prepolymers are conventionally based upon hydroxy terminated polyethers or polyesters which are polyisocyanate endcapped and then reacted with sufficient acrylate or methacrylate hydroxy ester to react with substantially all the free isocyanate functions.

The photosensitizers used in such systems are well-known in the art. Benzoin ethers are convenient for such use.

The compounds of Formula I, when blended in conventional fashion into these formulations, function as viscosity lowering agents and introduce greater flexibility and extensibility into cured films prepared from these blended formulations.

The coating and curing of these blends onto any desired substrate is, as will be obvious, performed in conventional fashion as outlined hereinabove for the formulations of compounds of Formula I themselves.

The following examples further illustrate the best mode contemplated by the inventor for the practice of his invention.

EXAMPLE 1

Dithiodiglycol Diacrylate

A mixture of dithiodiglycol (1 mole), ethyl acrylate (5.5 moles), phenothiazine (0.224 g), and nitrobenzene (0.112 g) is heated to reflux while sparging the mixture with air using a very low air flow. A small quantity of the vapor condensate is collected and removed to assure dryness. After cooling, triisopropyl titanate (Tyzor TPT) (5.6 g) is added and the mixture again heated to reflux while maintaining a low flow air sparge of the mixture. The mixture is heated at reflux while collecting the vapor condensate and removing it from the reaction. The first fraction (100 ml) is collected at a pot temperature of 90°–100.5° C. and a vapor temperature of 79°–87° C.

The second fraction (102 ml) is collected at a pot temperature of 101°–105° C. vapor temperature 81°–87° C., the third fraction (120 ml) is collected at a pot temperature of 107°–115° C., vapor temperature 84°–87° C. The fourth fraction (100 ml) is collected at pot temperature 69°–94° C., vapor temperature 40°–52.5° C. under 300–335 mm Hg vacuum.

The remaining ethyl acrylate is then stripped under vacuum at 1.8–2.0 mm Hg. The residue in the reaction vessel is filtered to give the title product as a clear amber low viscosity liquid (248.9 g).

Analysis for $C_{10}H_{14}S_2O_4$: Calculated: C, 45.8%, H, 5.34%; S 24.4%. Found: C, 45.9%, H, 5.97%; S 24.97%.
Acid No.: 0.81; OH No. 1.17; % Unsat. 0.6582
An aliquot is washed with distilled water and dried.
Acid No.: 0.49; OH No. 1.0; % Unsat. 0.665.

EXAMPLE 2

Radiation curable polymer formulations are prepared based upon an ethyl acrylate terminated urethane prepolymer prepared by endcapping an 80/20 ethylene glycol/propylene glycol adipate polyester polyol with toluene diisocyanate to an NCO content of 1.65% and then endcapping with hydroxy ethyl acrylate. The formulations are as shown in Table I.

TABLE I

| Material | Sample No. Quantity parts by weight (pbw) | | | |
|---|---|---|---|---|
| | 1 | 2 | 3 | 4 |
| Ethylacrylate terminated urethane prepolymer | 40 | 40 | 35 | 35 |
| 1,6-hexanediol diacrylate | 10 | — | 15 | — |
| Dithiodiglycol diacrylate | — | 10 | — | 15 |
| Vicure 10* | 1.0 | 1.0 | 1.0 | 1.0 |
| UCCL 7602** | 0.5 | 0.5 | 0.5 | 0.5 |

*Vicure 10 is a liquid benzyl ether photosensitizer sold by Stauffer Chemical Co.
**UCCL 7602 is modified silicone flow control agent sold by Union Carbide.

The blended mixtures are cast in a 10 mil thick film on silicone release paper and cured at speeds of 20, 40 or 60 feet per minute using a QC 1202 AN Processor (PPG Industries Inc., Radiation Polymer Co.) under two 12 in. lamps having a linear power density of 200 watts per inch.

The viscosities of blends 1, 2 and 4 were greater than 14,800 centistokes prior to cure, while that of blend 3 was between 9850 and 14,800 centistokes.

There were a few fish eyes and an orange peel effect to all the films cure at 20 feet per minute gave no cotton effect on blends 1, 3 and 4 and very slight cotton on blend 2. Cure at 40 feet per minute gave some cotton for blend 1, slight cotton for blends 2 and 3 and very slight trace of cotton for blend 4. Much cotton effect was noted for blend 1 at 60 feet per minute while blend 2 had slight cotton, blend 3 had some cotton, and blend 4 a very slight trace of cotton. Blends 1 and 3 had strong sweet odors after cure, while blends 2 and 4 had strong odors. The physical properties of the cured films are given in Table II.

TABLE II

| | Blend | | | |
|---|---|---|---|---|
| | 1 | 2 | 3 | 4 |
| Tensile (psi) | 945 | 810 | 1170 | 1180 |
| Elongation (%) | 40 | 60 | 25 | 45 |
| Modulus (25%) | 550 | 240 | 1170 | 615 |

TABLE II-continued

| | Blend | | | |
|---|---|---|---|---|
| | 1 | 2 | 3 | 4 |
| (50%) | — | 595 | — | — |

The subject matter which Applicant regards as his invention is particularly pointed out and distinctly claimed as follows:

1. A curable composition which comprises an acrylate terminated polyurethane prepolymer, a photosensitizer, and a compound of the formula

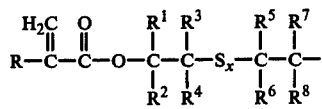

wherein R is hydrogen or methyl, $R^1$, $R^2$, $R^3$, $R^4$, $R^5$, $R^6$, $R^7$ and $R^8$ are hydrogen, methyl or ethyl, or each independently is hydrogen, methyl, ethyl, or chloromethyl, $x$ is from about 2 to about 4, $y$ is 0 or an integer of from 1 to 3, and $z$ is 0 or is sufficient to make a molecular weight of about 4000.

2. A process for the preparation of a UV curable composition based on an acrylate terminated polyurethane prepolymer, having improved extensibility and flexibility which comprises blending:
   (a) an acrylate terminated polyurethane prepolymer;
   (b) a photosensitizer; and
   (c) a compound as defined in claim 1.

3. An article of manufacture which comprises a substrate coated on at least one surface with a coating comprising the actinic radiation induced reaction products of
   (a) an acrylate terminated polyurethane prepolymer;
   (b) a photosensitizer; and
   (c) a compound as defined in claim 1.

* * * * *

REEXAMINATION CERTIFICATE (610th)

United States Patent [19]

Bertozzi

[11] B1 4,131,716

[45] Certificate Issued  Dec. 30, 1986

[54] ACRYLIC ACID ESTERS OF POLYTHIODIALKANOLS AND RELATED COMPOUNDS

[75] Inventor: Eugene R. Bertozzi, Yardley, Pa.

[73] Assignee: Thiokol Corporation, Newtown, Pa.

Reexamination Request:
No. 90/001,025, Jun. 5, 1986

Reexamination Certificate for:
Patent No.: 4,131,716
Issued: Dec. 26, 1978
Appl. No.: 791,756
Filed: Apr. 28, 1977

[51] Int. Cl.⁴ .................... C08F 2/50; C08F 236/02

[52] U.S. Cl. .................. 428/423.1; 427/54.1; 428/425.5; 428/522; 428/424.4; 525/455; 522/96; 526/311; 560/222

[58] Field of Search ............. 522/96; 428/425.1, 425.5

[56] References Cited

PUBLICATIONS

A. M. Rabie, *European Polymer Journal* vol. 8, pp. 687–695 "Synthesis and Characterization of some Polyfunctional Thioalkylene Acrylate Monomers and Their Polymers–I" (1972).

A. A. Berlin, A. M. Rabia, Vysokomol. Soedin., Ser. B (1973), vol. 15, No. 6, pp. 416–419.

*Primary Examiner*—Wilbert J. Briggs

[57] ABSTRACT

Diacrylate esters of dithiodiglycol and of polyether and polyformal oligomers thereof, their preparation, and use in combination with other radiation curable prepolymers for preparation of radiation curable compositions are disclosed.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2 and 3, dependent on an amended claim, are determined to be patentable.

New claims 4–6 are added and determined to be patentable.

1. A curable composition which comprises an acrylate terminated polyurethane prepolymer, a photosensitizer, and a compound of the formula

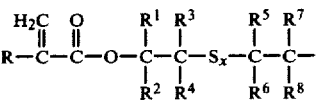

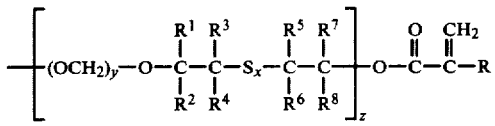

wherein R is hydrogen or methyl, $R^1$, $R^2$, $R^3$, $R^4$, $R^5$, $R^6$, $R^7$ and $R^8$ are hydrogen, methyl, [or] ethyl, *or chloromethyl,* or each independently is hydrogen, methyl, ethyl, or chloromethyl, x is from about 2 to about 4, y is 0 or an integer of from 1 to 3, and z is [0 or is] *a non-zero number* sufficient to make a molecular weight of *up to* about 4000.

*4. A composition according to claim 1 wherein y is an integer from 1 to 3.*

*5. A process according to claim 2 wherein y is an integer from 1 to 3.*

*6. An article according to claim 3 wherein y is an integer from 1 to 3.*

* * * * *